United States Patent [19]

Samaritani

[11] Patent Number: 5,898,030
[45] Date of Patent: Apr. 27, 1999

[54] HGH CONTAINING PHARMACEUTICAL COMPOSITIONS

[75] Inventor: Fabrizio Samaritani, Rome, Italy

[73] Assignee: Applied Research Systems Ars Holding N.V, Netherlands

[21] Appl. No.: 08/750,684

[22] PCT Filed: Jun. 17, 1994

[86] PCT No.: PCT/IT94/00086

§ 371 Date: Dec. 17, 1996

§ 102(e) Date: Dec. 17, 1996

[87] PCT Pub. No.: WO95/35116

PCT Pub. Date: Dec. 28, 1995

[51] Int. Cl.[6] .......................... A61K 38/27; C07K 14/61
[52] U.S. Cl. ..................... 514/12; 530/399; 930/120
[58] Field of Search ................ 514/2, 8, 12; 530/399

[56] References Cited

U.S. PATENT DOCUMENTS 5,096,885   3/1992  Pearlman et al. ................... 514/12
5,122,367   6/1992  Ron et al. ........................... 424/80

FOREIGN PATENT DOCUMENTS 210039      1/1987    European Pat. Off. .
1326439     1/1994    European Pat. Off. .
89 09614   10/1989    WIPO .
WO 94/03198 2/1994   WIPO .

OTHER PUBLICATIONS

M.J. Pickal, "Freeze–Drying of Proteins, Part II: Formulation Selection", *Biopharm,* vol. 3, No. 9, Oct. 1990, pp. 26–30.

*Primary Examiner*—John Ulm
*Assistant Examiner*—Christine Saoud
*Attorney, Agent, or Firm*—Ostrolenk, Faber, Gerb & Soffen, LLP

[57] ABSTRACT

Pharmaceutical compositions containing hGH stabilized by means of saccharose. The formulation is particularly suitable for stabilizing a lyophilisate of recombinant hGH.

20 Claims, No Drawings

HGH CONTAINING PHARMACEUTICAL COMPOSITIONS

This is the national stage corresponding to PCT/IT94/00086, filed Jun. 17, 1994.

BACKGROUND OF THE INVENTION

The present invention concerns human growth hormone (hGH) containing pharmaceutical compositions. More precisely, it concerns compositions of saccharose-stabilized human growth hormone. It is known that the highly purified proteins are time-unstable and are stabilized, for instance, in admixture with saccharides, such as lactose and mannitol, or else with proteins and aminoacids, such as albumin and glycin.

Human growth hormone is secreted in the human pituitary. In its mature form it consists of 191 amino acids, has a molecular weight of 22,000 and thus is more than three times as large as insulin. This hormone is a linear polypeptide containing two intrachain disulfide bridges. Until the advent of recombinant DNA technology, hGH could be obtained only by laborious extraction from a limited source: the pituitary glands of human cadavers. The consequent scarcity of substance limited its application to treatment of hypopituitary dwarfism even though it has been proposed to be effective in the treatment of burns, wound healing, dystrophy, bone knitting, diffuse gastric bleeding and pseudarthrosis. HGH can be produced in a recombinant host cell, in quantities which would be adequate to treat hypopituitary dwarfism and the other conditions for which it is effective.

The major biological effect of hGH is to promote growth. The organ systems affected include the skeleton, connective tissue, muscles and viscera such as liver, intestine and kidneys. Growth hormone exerts its action through interaction with specific receptors on cell membranes.

Compositions of lyophilised proteins are described in M. J. Pikal, Biopharm, October 1990, 25–30. There are reported examples of growth hormone formulations with stabilizing excipients such as mannitol, glycin, arginine and lactose.

In particular, the lyophilisation is described in the presence of various substances in their amorphous state, as sugars, which increase the collapse temperature and permit to obtain shorter lyophilisation times. However, it is not feasible, according to the author, to foresee a standard formulation for all the proteins, and the choice of the best formulation requires a remarkable selection work.

German patent DE 3520228 describes bioactive proteins, including growth hormone, in formulations which are stabilized by means of polysaccarides comprising repetitive maltotriose units.

WO 89/09614 describes formulations of human growth hormone stabilized with glycine, mannitol and a buffer, wherein the molar ratio of human growth hormone:glycine is 1:50–200.

U.S. Pat. No. 5,122,367 patent describes a controlled release system for administration of growth hormones, which comprises the protein and a polysaccaride incorporated within a polymeric matrix.

EP 210039 patent application describes a controlled release implant for subcutaneous administration to an animal of bovine or porcine growth hormone, in the form of a matrix containing 40% saccharose.

According to the present invention, hGH may be either natural or synthetic, i.e. produced on the basis of recombinant DNA technology, the latter being preferred.

The injectable formulations of human growth hormone are obtained by a process which includes their lyophilisation in order to obtain a dry powder. Human growth hormone is highly liable to denaturization during the lyophilisation process and it desirable to obtain stable formulations to maintain a longer cycle life when they are stored at room temperature.

In order that materials like hGH be provided to health care personnel and patients, these materials must be prepared as pharmaceutical compositions. Such compositions must maintain activity for appropriate periods of time, must be acceptable in their own right to easy and rapid administration to humans, and must be readily manufacturable. In many cases, pharmaceutical formulations are provided in frozen or in lyophilized form. In this case, the composition must be thawed or reconstituted prior to use. The frozen or lyophilized form is often used to maintain biochemical integrity and the bioactivity of the medicinal agent contained in the compositions under a wide variety of storage conditions, as it is recognized by those skilled in the art that lyophilized preparations often maintain activity better than their liquid counterparts. Such lyophilized preparations are reconstituted prior to use by the addition of suitable pharmaceutically acceptable diluent(s), such as sterile water for injection or sterile physiological saline solution, and the like.

Alternatively, the composition can be provided in liquid form appropriate for immediate use. Desirable is a liquid formulation which maintains its activity in long term storage.

Current formulation of hGH lose activity due to formation of dimer and higher order aggregates (macro range) during formulation processing as well as during storage and reconstitution. Other chemical changes, such as deamidation and oxidation may also occur upon storage.

Human growth hormone is found on the market in formulations stabilized for example with mannitol (Saizen® and Grorm® Serono).

SUMMARY OF THE INVENTION

I have now found that saccharose confers a better stability to the formulation of hGH and in particular to the form of this glycoprotein which has been prepared with the recombinant DNA technique. It has also been found that saccharose unexpectedly prevents the formation of a precipitate when the reconstituted solutions are shaken.

The main object of the present invention is to provide pharmaceutical compositions comprising a solid intimate mixture of human growth hormone and a stabilizing amount of saccharose, alone or in combination of other stabilizing agents.

A further object is to provide a process for the preparation of said pharmaceutical composition, comprising the step of lyophilising an aqueous solution of the components in the containers. Another object is to provide a presentation form of said pharmaceutical composition comprising the said solid mixture hermetically closed in a sterile condition within a container suitable for storage before use and suitable for reconstitution of the mixture for injectable substances.

An other object is to provide a solution for said solid mixture reconstituted into an injectable solution.

DESCRIPTION OF THE INVENTION

In order to evaluate the excipient's effect on the stability of the active ingredients, various formulations of recombinant hGH containing 5 or 10 mg pro vial have been prepared with various excipients: saccharose, glycin, mannitol, saccharose plus mannitol and mannitol plus glycin.

The compositions of the various formulations which have been prepared are reported in tables 1 and 4. The preparation of the lyophilisate was performed by diluting the bulk of hGH with solutions containing the stabilizers all of which in buffers at pH 7.5. The obtained solutions were filtered, brought to the final volume, filled into the various glass vials and lyophilized.

The study of the stability of such formulations stored at 4° C., 25° C., 37° C. and 50° C. for 24 weeks, was determined through: reverse phase HPLC (RP-HPLC) according to the method described by R. M. Riggin et al., Anal. Biochem., 167:199–209, 1987, and size exclusion HPLC (HPSEC) according to US Pharmacopeia Preview November–December 1990 pag. 1253–1261. The results are reported in tables 2–3 and 5–6 where the measure is expressed as per cent recovery of hGH in the various formulations.

The chromatographic assay methodology to evaluate the per cent recovery of hGH was carried out as described by Pikal in Pharmaceutical Research 8, pag. 428 "Assays".

In the preformulation phase, the effect of pH and of the buffer on the stability of the rhGH on freeze dried form was tested by evaluating the stability at 50° C. Tests were carried out on different buffer systems prepared with acetic acid, phosphoric acid, succinic acid 0.01M at pH 6.00, 7.00 and 8.00 with NaOH.

The results showed that while the rhGH stability was not affected by the buffer, the formulations were anyway more stable at about pH 8.00.

The selected pH for compositions was 7.5.

Seven freeze dried formulations at rhGH concentration of 5 mg/vial were then prepared, using both phosphate and succinate buffer at pH 7.5 to test the compatibility of the active drug with different excipients (saccharose 68.4 mg/vial, mannitol 36.8 mg/vial, mannitol/glycine 25+4 mg/vial, mannitol/saccharose 32+7.5 mg/vial). The amount of excipients was selected in order to have an isotonic solution after reconstitution with bacteriostatic solvent. The filling volume was 1 ml.

Samples, prepared under sterile conditions, were stored at 50° C., 37° C., 25° C. and 4° C. for 24 weeks and tested by HPSEC, Reverse phase HPLC. pH and moisture content were determined.

The stability of the reconstituted solutions with 0.3% m-cresol and 0.9% benzyl alcohol at 4° C. and 25° C. was also studied.

The HPSEC and RP HPLC were performed as described before.

The pH was determined by pH meter on one vial reconstituted with 1 ml of water for injection. To determine the moisture content of the lyophilized vials, the composition of one vial was suspended in 1 ml of 2-isopropanol, filtered through an Anotop 10, 0.22 μm Disposable filter (Merck) and injected in Metrohm Coulometer.

The results of stability, tested by RP-HPLC (Riggin's method), are reported in Table 2. The chromatographic profiles of the formulations containing saccharose (HGH/3 and HGH/7 of Table 1) after 24 weeks at 50° C. are not different from those obtained at time zero.

At the same temperature, a purity decrease of 13–22% was found in the formulations containing mannitol and mannitol+glycine.

Data reported in table 3 refer to the results obtained by HPSEC analyses. No decrease of rHGH purity percentage was found in all the tested formulations. No significant variation of the moisture content was observed during the study in all lyophilized tested formulations.

A decrease of pH was observed at 37° C. and 50° C. for lots HGH/5 and HGH/7 of Table 1.

The stability of the reconstituted solutions was also studied through RP-HPLC (Riggin's method) and HPSEC analyses.

With RP-HPLC method, after five weeks at 25° C. the purity decrease was found to be in the range of 30%–50% for samples reconstituted both with benzyl alcohol and with m-cresol. After seven weeks at 4° C., the variation was of about 14% in presence of benzyl alcohol and 4%–8% with m-cresol.

No variation was observed at 4° C. with HPSEC method; on the contrary, a decrease of rHGH purity of about 5% was found at 25° C. for all the formulations in presence both of benzyl alcohol and m-cresol.

Results showed that formulations containing saccharose and saccharose+mannitol presented a better stability profile when compared to the other formulations.

On the basis of the results obtained with the 5 mg compositions, saccharose and mannitol were chosen for the preparation of five freeze dried formulations (Table 4) contained 10 mg hGH/vial using phosphate and succinate buffer at pH 7.5 adjusted with NaOH 2.5M. One formulation contained 68.4 mg/vial of saccharose (filling volume 1 ml) in phosphate buffer only, the others containing 102.6 mg/vial of saccharose (filling volume 1.5 ml) and mannitol+saccharose 130+40 mg/vial (filling volume 1.5 ml), both in phosphate and succinate buffer. The optimal ratio between saccharose and mannitol and the filling volume to obtain a product with good physical characteristics was adjusted on the basis of preliminary freeze drying trials. The optimum ratio mannitol/saccharose in terms of freeze dried-cake resistance to high temperature was 3:1 and the maximum volume to be freezed dried was 1.5 ml.

The formulations were submitted to stability tests by storing samples at 50° C., 37° C., 25° C. and 4° C. for 24 weeks. Samples were submitted to the following analytical controls: HPSEC, RP-HPLC (Riggin's method), pH and moisture content.

The stability of the reconstituted solutions with 0.3% m-cresol and 0.9% benzyl alcohol at 4° C. was monitored for 4 weeks. Samples were submitted to the same controls performed on the 5 mg dosage as described before. The analyses showed the following results: The formulations containing 68.4 mg/vial and 102.6 mg/vial of saccharose in succinate buffer tested by RP-HPLC analyses, did not show decrease of purity after 24 weeks storage at all the tested temperatures the results are reported in Table 5. The formation of degradation products was observed in the other formulations even after 4/6 weeks storage at 50° C.

No decrease of rHGH purity percentage was found in all tested formulations by HPSEC analyses, see Table 6. During the study no variation of pH and moisture content was observed in all the tested formulations.

Studies on the reconstituted solutions containing only saccharose were also performed by RP-HPLC (Riggin's method) and HPSEC analyses.

After 4 weeks at 4° C., with RP-HPLC method, the purity decrease was found to be of about 12% in presence of benzyl alcohol and 4% with m-cresol. No decrease of rHGH purity was observed at 4° C., with HPSEC method, in presence both of benzyl alcohol and m-cresol.

To valuate the efficacy of antimicrobial preservation, vials of HGH/3 formulation of Table 1, were reconstituted with 1 ml of bacteriostatic solvent (m-cresol 0.3% or benzyl alcohol 0.9%). They were tested according to European Pharmacopeia up to 21 days from seeding. Results are reported in tables 7 and 8.

The minimum acceptable efficacy (Minimum criteria) was reached for both the preservative solutions. The results obtained at zero time, in which the microorganisms were counted after spiking in both saline (NaCl 0.9%) and bacteriostatic solution, seem to indicate a higher efficacy of m-cresol vs benzyl alcohol mainly for Staphylococcus and pseudomonas that were reduced immediately after spiking from 90.000 to 25.000 and from 78.000 to 8.000 UFC/ml, respectively (Table 7).

Furthermore, the Aspergillus disappeared in m-cresol after 14 days from seeding (Table 8) and Pseudomonas after 6 hrs.

The above results indicate that the formulation containing 68.4 mg of saccharose, phosphate buffer at pH 7.5, filling volume 1 ml reconstituted with meta-cresol 0.3% is the one that guarantees the best stability of r-HGH both at 5 and 10 mg strength.

EXAMPLE OF PHARMACEUTICAL MANUFACTURING

Materials: pure saccharose Ph Eur, BP, Nord, NF (mercK); $H_3PO_4$ Suprapur (Merck); NaOH for analysis use (Merck); water for injectable.

As containers have been used vials DIN 2R (borosilicate glass type I), rubber closures (Pharmagummi W1816 V50) and Aluminium rings and Flip-off caps (Pharma-Metal GmbH).

Preparation of rHGH solution containing saccharose (for 1000 vials containing each 10 mg hGH).

Saccharose (68.4 g), $H_3PO_4$ (1.96 g) are dissolved into water for injectables (800 ml) in order to obtain the starting saccharose solution. The bulk of the hGH (10 g) is added to the saccharose solution that, after the pH has been adjusted at 7.5 by means of 2.5M NaOH, is brought to the final volume of 1000 ml. The solution is filtered through a 0.22 um Durapore sterile filter (Millipore). During the process the solution temperature is kept between 4° and 8° C. The solutions containing different excipients or a different active drug dosage have been prepared in a similar manner.

Filling up and lyophilisation

The vials are filled up with 1 ml of HGH sterile solution, transferred to the freeze dryer and cooled at −45° C. for 6 hrs. at least. The lyophilisation is started at the temperature of −45° C. with a vacuum of 0.07 mBar. The heating is performed according to the following scheme: +10° C. for 12 hrs.; then +35° C. until the end of the cycle.

TABLE 1

5 mg VIAL COMPOSITION

|  | HGH/1 | HGH/2 | HGH/3 | HGH/4 | HGH/5 | HGH/6 | HGH/7 |
|---|---|---|---|---|---|---|---|
| Components: | | | | | | | |
| r-HGH mg/vial Lot. n. PGRR920 1D1 | 5 | 5 | 5 | 5 | 5 | 5 | 5 |
| Saccharose mg/vial | 7.5 | — | 68.4 | — | 7.5 | — | 68.4 |
| Mannitol mg/vial | 32 | 36.4 | — | 25 | 32 | 36.4 | — |
| Glycine mg/vial | — | — | — | 5 | — | — | — |
| Buffer: | | | | | | | |
| Phosphoric Acid mg/vial | 0.98 | 0.98 | 0.98 | 0.98 | — | — | — |
| Succinic Acid mg/vial | — | — | — | — | 1.18 | 1.18 | 1.18 |
| NaOH q.s. to pH | 7.5 | 7.5 | 7.5 | 7.5 | 7.5 | 7.5 | 7.5 |
| Filling volume | 1 ml | 1 ml | 1 ml | 1 ml | 1 ml | 1 ml | 1 ml |
| Reconstitution volume | 1 ml | 1 ml | 1 ml | 1 ml | 1 ml | 1 ml | 1 ml |

TABLE 2

SAIZEN ® 5 mg
r-HGH CHROMATOGRAPHIC PURITY by RIGGIN'S METHOD

|  | 4° C. | | | | | | 25° C. | | | 37° C. | | | | FREEZE-DRIED FORMULATIONS 50° C. | | | | |
|---|---|---|---|---|---|---|---|---|---|---|---|---|---|---|---|---|---|---|
|  | T = 0 | 1 W | 2 W | 4 W | 8 W | 24 W | 4 W | 8 W | 24 W | 1 W | 4 W | 8 W | 24 W | 1 W | 2 W | 4 W | 8 W | 24 W |
| HGH/1 (M/S) | 94.63 | 95.65 | — | — | 94.51 | 95.74 | 94.35 | 94.71 | 95.83 | 95.07 | 95.15 | 93.53 | — | 94.95 | 94.45 | 93.62 | 92.6 | 92.86 |
| HGH/2 (M) | 94.75 | 96.09 | — | — | 90.59 | 92.13 | 94.32 | 92.97 | 92.21 | 94.09 | 92.48 | 88.83 | — | 92.05 | 89.00 | 87.97 | 83.41 | 72.3 |
| HGH/3 (S) | 94.44 | 95.38 | — | — | 95.16 | 96.28 | 94.66 | 94.98 | 96.41 | 95.10 | 95.52 | 94.43 | — | 95.06 | 95.04 | 94.4 | 94.66 | 95.69 |
| HGH/4 (M/G) | 94.57 | 95.40 | — | — | 93.14 | 93.65 | 94.56 | 93.59 | 93.98 | 94.59 | 93.85 | 90.81 | — | 93.09 | 91.72 | 88.78 | 85.89 | 72.22 |
| HGH/5 (M/S) | 94.25 | 95.45 | — | — | 94.04 | 95.02 | 94.77 | 94.28 | 94.59 | 94.56 | 94.39 | 92.57 | — | 94.10 | 93.09 | 92.34 | 91.93 | 90.27 |
| HGH/6 (M) | 94.29 | 95.50 | — | — | 92.50 | 93.74 | 94.09 | 93.56 | 94.13 | 93.99 | 91.74 | 91.11 | — | 92.65 | 91.25 | 89.58 | 87.94 | 81.62 |
| HGH/7 (S) | 94.15 | 95.00 | — | — | 95.37 | 96.15 | — | 94.99 | 96.46 | 94.55 | 94.39 | 94.52 | — | 94.67 | 94.93 | 94.49 | 94.54 | 95.70 |

M/S = Mannitol + Saccharose
M = Mannitol
M/G = Mannitol + Glycine
S = Saccharose
W = Week

TABLE 3 rHGH CHROMATOGRAPHIC PURITY by HPSEC

FREEZE-DRIED FORMULATIONS

| | T = 0 | 4° C. | | | | | 25° C. | | | 37° C. | | | | 24 W | 50° C. | | | | | |
|---|---|---|---|---|---|---|---|---|---|---|---|---|---|---|---|---|---|---|---|---|
| | | 1 W | 2 W | 4 W | 8 W | 24 W | 4 W | 8 W | 24 W | 1 W | 4 W | 8 W | 12 W | | 1 W | 2 W | 4 W | 8 W | 12 W | 24 W |
| HGH/1 (M/S) | 97.56 | 97.98 | — | — | 98.09 | 98.68 | 97.24 | 98.54 | 98.38 | 96.94 | 98.31 | 98.20 | 98.32 | — | 98.24 | 97.93 | 98.24 | 97.76 | 97.66 | 98.01 |
| HGH/2 (M) | 97.64 | 97.95 | — | — | 97.04 | 98.24 | 98.11 | 98.45 | 98.28 | 97.30 | 97.77 | 98.04 | 97.07 | — | 98.05 | 97.64 | 97.91 | 95.19 | 97.14 | 97.02 |
| HGH/3 (S) | 97.75 | 97.96 | — | — | 98.20 | 98.40 | 97.15 | 98.49 | 98.43 | 97.70 | 98.12 | 98.24 | 98.52 | — | 98.29 | 97.90 | 98.44 | 98.06 | 98.33 | 98.50 |
| HGH/4 (M/G) | 96.55 | 96.90 | — | — | 96.10 | 98.29 | 98.14 | 98.48 | 98.60 | 96.58 | 98.16 | 97.96 | 97.26 | — | 98.40 | 98.12 | 98.26 | 96.52 | 96.46 | 96.82 |
| HGH/5 (M/S) | 97.41 | 97.99 | — | — | 98.28 | 98.35 | 97.88 | 98.50 | 98.61 | 97.67 | 98.25 | 98.15 | 98.08 | — | 98.24 | 98.09 | 98.44 | 98.12 | 98.00 | 98.20 |
| HGH/6 (M) | 97.45 | 97.99 | — | — | 97.84 | 97.86 | 98.07 | 98.52 | 98.44 | 97.59 | 97.86 | 98.08 | 98.02 | — | 98.00 | 96.85 | 97.81 | 96.34 | 96.98 | 96.79 |
| HGH/7 (S) | 97.60 | 97.94 | — | — | 98.31 | 98.47 | 98.10 | 98.47 | 98.51 | 97.80 | 98.09 | 98.31 | 98.21 | — | 98.22 | 98.26 | 98.47 | 98.21 | 98.11 | 98.35 |

M/S = Mannitol + Saccharose
M = Mannitol
M/G = Mannitol + Glycine
S = Saccharose
W = Week

TABLE 4

10 mg VIAL COMPOSITION

| | S10/S/F/1/01 | S10/S/F/01 | S10/S/S/01 | S10/SM/F/01 | S10/SM/S/0 |
|---|---|---|---|---|---|
| Components: | | | | | |
| r-HGH mg/vial Lot. n. PGRR920 1D2 | 10 | 10 | 10 | 10 | 10 |
| Saccharose mg/vial | 68.4 | 102.6 | 102.6 | 40 | 40 |
| Mannitol mg/vial | — | — | — | 130 | 130 |
| Buffer: | | | | | |
| Phosphoric Acid mg/vial | 1.98 | 1.98 | — | 1.98 | — |
| Succinic Acid mg/vial | — | — | 2.36 | — | 2.36 |
| NaOH q.s. to pH | 7.5 | 7.5 | 7.5 | 7.5 | 7.5 |
| Filling volume | 1 ml | 1.5 ml | 1.5 ml | 1.5 ml | 1.5 ml |
| Reconstitution volume | 2 ml | 2 ml | 2 ml | 2 ml | 2 ml |

TABLE 5 rHGH CHROMATOGRAPHIC PURITY by RP-HPLC (RIGGIN'S METHOD)

FREEZE-DRIED FORMULATIONS

| | T = 0 | 4° C. | | | 25° C. | | | | 37° C. | | | | 50° C. | | | |
|---|---|---|---|---|---|---|---|---|---|---|---|---|---|---|---|---|
| | | 4 W | 6 W | 8 W | 4 W | 6 W | 8 W | 24 W | 4 W | 6 W | 8 W | 24 W | 4 W | 6 W | 8 W | 24 W |
| S10/S/S/01 | 95.87 | — | — | 96.08 | 95.61 | 95.68 | 95.28 | 96.60 | 95.16 | 95.66 | 95.93 | 96.11 | 94.75 | 94.99 | 94.89 | 93.74 |
| S10/S/F/1/01 | 95.65 | — | — | 95.01 | 95.36 | 95.65 | 95.92 | 94.69 | 94.91 | 95.48 | 95.40 | 94.62 | 94.17 | 94.43 | 94.45 | 94.31 |
| S10/S/F/01 | 95.34 | — | — | 95.93 | 95.13 | 95.57 | 95.08 | — | 94.32 | 94.50 | 93.41 | 92.46 | 92.13 | 91.47 | 89.75 | — |
| S10/SM/S/01 | 95.52 | — | — | 95.86 | 95.83 | 95.32 | 95.35 | 93.38 | 94.20 | 94.69 | 94.50 | 92.83 | — | 84.81 | — | — |
| S10/SM/F/01 | 95.23 | — | — | 95.70 | 94.44 | 94.94 | 95.24 | 90.04 | 92.51 | 92.76 | 90.74 | — | 87.92 | 85.29 | 82.03 | — |

S10/S/S/01 = SACCHAROSE/SUCCINATE (FILLING VOLUME 1.5 ml)
S10/S/F/1/01 = SACCHAROSE/PHOSPHATE (FILLING VOLUME 1 ml)
S10/S/F/01 = SACCHAROSE/PHOSPHATE (FILLING VOLUME 1.5 ml)
S10/SM/S/01 = SACCHAROSE + MANNITOL/SUCCINATE (FILLING VOLUME 1.5 ml)
S10/SM/F/01 = SACCHAROSE + MANNITOL/PHOSPHATE (FILLING VOLUME 1.5 ml)

TABLE 6 rHGH CHROMATOGRAPHIC PURITY by HPSEC

FREEZE-DRIED FORMULATIONS

| | | 4° C. | | | 25° C. | | | | 37° C. | | | | 50° C. | | | |
|---|---|---|---|---|---|---|---|---|---|---|---|---|---|---|---|---|
| | T = 0 | 4 W | 6 W | 8 W | 4 W | 6 W | 8 W | 24 W | 4 W | 6 W | 8 W | 24 W | 4 W | 6 W | 8 W | 24 W |
| S10/S/S/01 | 98.20 | — | — | 97.93 | 98.41 | 98.17 | 98.98 | 96.27 | 97.97 | 98.17 | 98.09 | 98.17 | 97.98 | 97.84 | 97.93 | 98.19 |
| S10/S/F/1/01 | 98.23 | — | — | 98.04 | 98.28 | 98.34 | 98.26 | 98.33 | 98.28 | 98.56 | 96.01 | 98.24 | 97.98 | 98.20 | 97.57 | 98.07 |
| S10/S/F/01 | 98.13 | — | — | 97.81 | 98.24 | 96.17 | 98.07 | — | 98.05 | 98.50 | 97.90 | 98.01 | 97.33 | 97.82 | 97.50 | 98.01 |
| S10/SM/S/01 | 97.97 | — | — | 97.82 | 98.19 | 96.32 | 98.22 | 98.30 | 96.62 | 98.14 | 98.17 | 97.76 | 97.61 | 97.22 | 97.93 | — |
| S10/SM/F/01 | 98.17 | — | — | 97.78 | 97.98 | 98.35 | 98.21 | 97.61 | 97.94 | 98.19 | 97.26 | — | 97.34 | 96.87 | 96.72 | — |

S10/S/S/01 = Saccharose/Succinate (filling volume 1.5 ml)
S10/S/F/1/01 = Saccharose/Phosphate (filling volume 1.0 ml)
S10/S/F/01 = Saccharose/Phosphate (filling volume 1.5 ml)
S10/SM/S/01 = Saccharose + Mannitol/Succinate (filling volume 1.5 ml)
S10/SM/F/01 = Saccharose + Mannitol/Phosphate (filling volume 1.5 ml)

TABLE 7

Efficacy of antimicrobial preservation. Benzyl Alcohol 0.9% was used as antimicrobial preservative (PRES) in hGH formulated vials (SAIZEN ®). The test was carried out according to the European Pharmacopeia and followed up to 21 days from seeding. The log. reduction was calculated vs the UFC counted at Zero time (ZT) in the preservative solution.

| | ZT | | 6 hrs | | 24 hrs | | 7 DAYS | | 14 DAYS | | 21 DAYS | |
|---|---|---|---|---|---|---|---|---|---|---|---|---|
| MICRORGAN-ISMS | SALINE UFC/ml | PRES. UFC/ml | UFC/ml | lg RED. vs PRES | UFC/ml | lg RED. vs PRES | UFC/ml | lg RED. vs PRES | UFC/ml | lg RED. vs PRES | UFC/ml | lg RED. vs PRES |
| STAPHYLOCOCCUS AUREUS | 90000 | 85000 | 0 | >3 | 80 | >3 | 0 | >3 | 0 | >3 | 0 | >3 |
| PSEUDOMONAS AERUGINOSA | 78000 | 48000 | 18000 | 0.4 | 0 | >3 | 0 | >3 | 0 | >3 | 0 | >3 |
| CANDIDA ALBICANS | 92000 | 36000 | N.T. | — | N.T. | — | 0 | >3 | 0 | >3 | 0 | >3 |
| ASPERGILLUS NIGER | 98000 | 75000 | N.T. | — | N.T. | — | 4000 | 1.3 | 300 | 2.4 | 200 | 2.6 |

N.T. = not tested

TABLE 8

Efficacy of antimicrobial preservation. M-Cresol 0.3% was used as antimicrobial preservative (PRES) in hGH formulated vials (SAIZEN ®). The test was carried out according to the European Pharmacopeia and followed up to 21 days from seeding. The log. reduction was calculated vs the UFC counted at Zero time (ZT) in the preservative solution.

| | ZT | | 6 hrs | | 24 hrs | | 7 DAYS | | 14 DAYS | | 21 DAYS | |
|---|---|---|---|---|---|---|---|---|---|---|---|---|
| MICRORGAN-ISMS | SALINE UFC/ml | PRES. UFC/ml | UFC/ml | lg RED. vs PRES | UFC/ml | lg RED. vs PRES | UFC/ml | lg RED. vs PRES | UFC/ml | lg RED. vs PRES | UFC/ml | lg RED. vs PRES |
| STAPHYLOCOCCUS AUREUS | 90000 | 25000 | 1000 | 1.4 | 0 | >3 | 0 | >3 | 0 | >3 | 0 | >3 |
| PSEUDOMONAS AERUGINOSA | 78000 | 8000 | 0 | >3 | 0 | >3 | 0 | >3 | 0 | >3 | 0 | >3 |
| CANDIDA ALBICANS | 92000 | 60000 | N.T. | — | N.T. | — | 0 | >3 | 0 | >3 | 0 | >3 |
| ASPERGILLUS NIGER | 98000 | 78000 | N.T. | — | N.T. | — | 3000 | 1.4 | 0 | >3 | 0 | >3 |

N.T. = not tested

I claim:

1. A pharmaceutical composition consisting essentially of a solid intimate mixture of human growth hormone (hGH) and a stabilizing amount of a stabilizer selected from the group consisting of saccharose and a combination of saccharose and mannitol.

2. A pharmaceutical composition according to claim 1, wherein the solid intimate mixture is a lyophilisate.

3. A pharmaceutical composition according to claim 1, wherein the hGH is recombinant.

4. A pharmaceutical composition according to claim 1, containing 5 or 10 mg of hGH.

5. A pharmaceutical composition according to claim 1, wherein the stabilizer is saccharose.

6. A pharmaceutical composition according to claim 1, wherein the stabilizer is a combination of saccharose and mannitol.

7. A process for preparing a pharmaceutical composition according to claim 1 comprising providing an aqueous solution of human growth hormone and a stabilizing amount of saccharose, placing the aqueous solution in a container and lyophilizing the solution in the container.

8. The process according to claim 7, wherein the aqueous solution is a buffer solution selected from the group consisting of acetate buffer, succinate buffer and phosphate buffer.

9. The process according to claim 8, wherein the buffer solution is phosphate buffer.

10. The process according to claim 8, wherein the pH of the solution is within the range 6.0 to 8.0.

11. A process according to claim 8, wherein the pH of the solution is 7.5.

12. A solution comprising the pharmaceutical composition according to claim 1, reconstituted in a solvent or a solution for injectables.

13. A reconstituted solution, according to claim 12, comprising 5 or 10 mg/vial of hGH, 68.4 mg/vial of saccharose and phosphate buffer at pH 7.5.

14. A solution according to claim 13, wherein the solvent is a bacteriostatic solvent.

15. A solution according to claim 14, wherein the bacteriostatic solvent is 0.3% m-cresol.

16. A hermetically sealed sterile container containing the pharmaceutical composition of claim 1 therein.

17. A hermetically sealed sterile container according to claim 16 wherein the pharmaceutical composition is a lyophilisate.

18. A hermetically sealed sterile container according to claim 16 wherein the hGH is recombinant.

19. A hermetically sealed sterile container according to claim 16 containing 5–10 mg of hGH.

20. A pharmaceutical composition consisting of a solid intimate mixture of human growth hormone (hGH) and a stabilizing amount of a stabilizer selected from the group consisting of saccharose and a combination of saccharose and mannitol.

* * * * *